United States Patent
Margaria et al.

(10) Patent No.: US 10,398,867 B2
(45) Date of Patent: Sep. 3, 2019

(54) DETERMINING INFORMATION ABOUT A PATIENTS FACE

(71) Applicant: Koninklijke Philips N.V., Eindhoven (NL)

(72) Inventors: Elizabeth Powell Margaria, Pittsburgh, PA (US); Jonathan Sayer Grashow, Pittsburgh, PA (US); Rudolf Maria Jozef Voncken, Eindhoven (NL); Dmitry Nikolayevich Znamenskiy, Eindhoven (NL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 222 days.

(21) Appl. No.: 15/348,528

(22) Filed: Nov. 10, 2016

(65) Prior Publication Data
US 2017/0128686 A1 May 11, 2017

Related U.S. Application Data

(60) Provisional application No. 62/253,214, filed on Nov. 10, 2015.

(51) Int. Cl.
*A61M 16/06* (2006.01)
*A61M 13/00* (2006.01)
(Continued)

(52) U.S. Cl.
CPC .............. *A61M 16/06* (2013.01); *A61B 1/24* (2013.01); *A61B 5/0053* (2013.01); *A61B 5/1077* (2013.01); *A61B 5/70* (2013.01); *A61B 90/13* (2016.02); *A61F 5/56* (2013.01); *A61M 13/003* (2013.01); *G06T 19/00* (2013.01); *G16H 50/50* (2018.01); *A61B 2034/105* (2016.02);
(Continued)

(58) Field of Classification Search
None
See application file for complete search history.

(56) References Cited

U.S. PATENT DOCUMENTS 7,827,038 B2 11/2010 Richard
2005/0083248 A1* 4/2005 Biocca ............... A41D 31/0088
345/8

(Continued)

FOREIGN PATENT DOCUMENTS

JP 2010131091 6/2010
WO WO2015092724 A1 6/2015

OTHER PUBLICATIONS

Hsu, Ding-Yang, Yih-Lin Cheng, Mauo-Ying Bien, and Hsin-Chien Lee. "Development of a method for manufacturing customized nasal mask cushion for CPAP therapy." Australasian physical & engineering sciences in medicine 38, No. 4 (2015): 657-664. (Year: 2015).*

*Primary Examiner* — Michelle M Entezari
(74) *Attorney, Agent, or Firm* — Michael W. Haas

(57) ABSTRACT

An electronic apparatus includes a compilation unit structured to receive a plurality of different 3-D models of a patient's face, to compare the different 3-D models of the patient's face and to determine additional information about the patient's face based on the comparison, wherein the additional information includes at least one of a location of hard tissue, a depth of soft tissue, and a compliance of soft tissue, and wherein the patient's face is manipulated between the different 3-D models.

21 Claims, 4 Drawing Sheets

(51) Int. Cl.
*A61B 90/13* (2016.01)
*A61B 1/24* (2006.01)
*A61B 5/107* (2006.01)
*A61B 5/00* (2006.01)
*A61B 34/10* (2016.01)
*A61F 5/56* (2006.01)
*G06T 19/00* (2011.01)
*G16H 50/50* (2018.01)

(52) U.S. Cl.
CPC .............. *A61M 2016/0661* (2013.01); *A61M 2205/3306* (2013.01); *A61M 2209/04* (2013.01)

(56) References Cited

U.S. PATENT DOCUMENTS

| | | | |
|---|---|---|---|
| 2009/0301482 A1* | 12/2009 | Burton | A61M 16/10 128/203.12 |
| 2011/0298912 A1* | 12/2011 | Jelinek | A61B 5/1171 348/78 |
| 2012/0300900 A1* | 11/2012 | Koivisto | A61B 5/0064 378/19 |
| 2012/0309520 A1* | 12/2012 | Evertt | G06T 19/20 463/31 |
| 2013/0147788 A1* | 6/2013 | Weise | G06T 13/40 345/419 |
| 2014/0278319 A1* | 9/2014 | Thiruvengada | G06F 17/5009 703/11 |
| 2014/0340397 A1* | 11/2014 | Lievens | G06T 19/20 345/420 |
| 2015/0045926 A1 | 2/2015 | Thornton | |
| 2015/0055085 A1* | 2/2015 | Fonte | G06Q 30/0621 351/178 |
| 2015/0157822 A1* | 6/2015 | Karpas | B29C 33/52 128/206.24 |
| 2015/0245890 A1* | 9/2015 | Wouters | A63B 71/085 700/98 |
| 2015/0250971 A1 | 9/2015 | Bachelder | |
| 2015/0265794 A1* | 9/2015 | De Kruyff | A61M 16/06 128/200.23 |
| 2016/0015924 A1* | 1/2016 | Harrison | A61M 16/0605 128/205.25 |
| 2016/0317264 A1* | 11/2016 | Derraugh | A61C 13/34 |
| 2017/0091994 A1* | 3/2017 | Beeler | G06T 17/20 |

* cited by examiner

US 10,398,867 B2

DETERMINING INFORMATION ABOUT A PATIENTS FACE

CROSS-REFERENCE TO RELATED APPLICATIONS

This patent application claims the priority benefit under 35 U.S.C. § 119(e) of U.S. Provisional Application No. 62/253,214 filed on Nov. 10, 2015, the contents of which are herein incorporated by reference.

BACKGROUND OF THE INVENTION

1. Field of the Invention

The present invention pertains to an electronic apparatus and method for determining additional information about a patient's face, and, in particular, to an electronic apparatus and method for determining information on at least one of a location of hard tissue and tissue compliance in a patient's face.

2. Description of the Related Art

Obstructive sleep apnea (OSA) is a condition that affects millions of people from around the world. OSA is characterized by disturbances or cessation in breathing during sleep. OSA episodes result from partial or complete blockage of airflow during sleep that lasts at least 10 seconds and often as long as 1 to 2 minutes. In a given night, people with moderate to severe apnea may experience complete or partial breathing disruptions as high as 200-500 per night. Because their sleep is constantly disrupted, they are deprived of the restorative sleep necessary for efficient functioning of body and mind. This sleep disorder has also been linked with hypertension, depression, stroke, cardiac arrhythmias, myocardial infarction and other cardiovascular disorders. OSA also causes excessive tiredness.

Non-invasive ventilation and pressure support therapies involve the placement of a patient interface device, which is typically a nasal or nasal/oral mask, on the face of a patient to interface the ventilator or pressure support system with the airway of the patient so that a flow of breathing gas can be delivered from the pressure/flow generating device to the airway of the patient.

Typically, patient interface devices include a mask shell or frame having a cushion attached to the shell that contacts the surface of the patient. The mask shell and cushion are held in place by a headgear that wraps around the head of the patient. The mask and headgear form the patient interface assembly. A typical headgear includes flexible, adjustable straps that extend from the mask to attach the mask to the patient.

Because patient interface devices are typically worn for an extended period of time, a variety of concerns must be taken into consideration. For example, in providing CPAP to treat OSA, the patient normally wears the patient interface device all night long while he or she sleeps. One concern in such a situation is that the patient interface device is as comfortable as possible, otherwise the patient may avoid wearing the interface device, defeating the purpose of the prescribed pressure support therapy. Additionally, an improperly fitted mask can cause red marks or pressure sores on the face of the patient. Another concern is that an improperly fitted patient interface device can include gaps between the patient interface device and the patient that cause unwanted leakage and compromise the seal between the patient interface device and the patient. A properly fitted patient interface device should form a robust seal with the patient that does not break when the patient changes positions or when the patient interface device is subjected to external forces. Thus, it is desirable to properly fit the patient interface device to the patient.

3D scanning can be employed in order to improve the fit of the patient interface device to the patient. Generally, a 3D scan can be taken of the patient's face and then the information about the patient's face can be used to select the best fitting patient interface device or to custom make a patient interface device that fits the patient well. However, the 3D scan only includes information on the external geometry of the patient's face. The patient's face is more complex than its exterior geometry. For example, the patient's face has underlying hard tissue and various thicknesses of soft tissue in different areas in the face. These characteristics can affect how well a patient interface device fits.

Accordingly, a need exists for improvement in optimizing the fit of a patient interface device for a patient.

SUMMARY OF THE INVENTION

In accordance with aspects of the disclosed concept, an electronic apparatus comprises a compilation unit structured to receive a plurality of different 3-D models of a patient's face, to compare the different 3-D models of the patient's face and to determine additional information about the patient's face based on the comparison, wherein the additional information includes at least one of a location of hard tissue, a depth of soft tissue, and a compliance of soft tissue and/or hard tissue, and wherein the patient's face is manipulated between the different 3-D models.

According to other aspects of the disclosed concept, a method of determining additional information about a patient's face comprises receiving a plurality of different 3-D models of the patient's face; comparing the different 3-D models of the patient's face; and determining the additional information about the patient's face based on the comparison, wherein the additional information includes at least one of a location of hard tissue, a depth of soft tissue, and a compliance of soft tissue and/or hard tissue, and wherein the patient's face is manipulated between the different 3-D models.

DETAILED DESCRIPTION OF EXEMPLARY EMBODIMENTS

Figure 1:
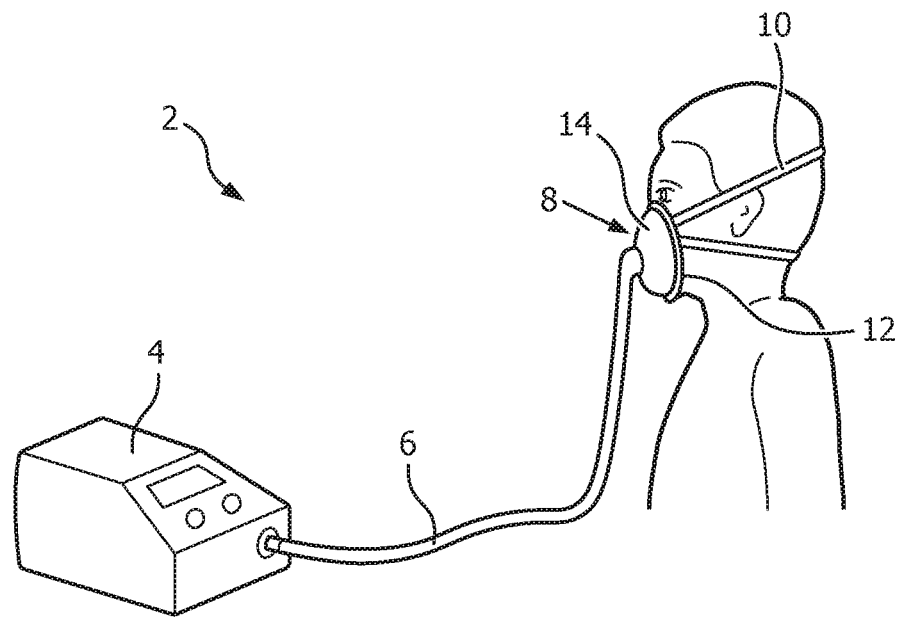
FIG. 1 is a schematic diagram of a system adapted to provide a regimen of respiratory therapy to a patient according to an exemplary embodiment of the disclosed concept.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

As employed herein, the terms "processor", "processing unit", and similar terms shall mean a programmable analog and/or digital device that can store, retrieve and process data; a controller; a control circuit; a computer; a workstation; a personal computer; a microprocessor; a microcontroller; a microcomputer; a central processing unit; a mainframe computer; a mini-computer; a server; a networked processor; or any suitable processing device or apparatus.

As employed herein, the term "addition information about a patient's face" means information in addition to the external geometry of the patient's face and includes information such as, without limitation, information on the location of hard tissue, information on the depth of soft tissue and information on the compliance of soft tissue.

A system 2 adapted to provide a regimen of respiratory therapy to a patient is generally shown in FIG. 1. System 2 includes a pressure/flow generator 4, a delivery conduit circuit 6, a patient interface device 8 and a headgear 10 for securing patient interface device 8 to the head of a patient (not numbered). Pressure generating device 4 is structured to generate a flow of breathing gas and may include, without limitation, ventilators, constant pressure support devices (such as a continuous positive airway pressure device, or CPAP device), variable pressure devices (e.g., BiPAP®, Bi-Flex®, or C-Flex™ devices manufactured and distributed by Philips Respironics of Murrysville, Pa.), and auto-titration pressure support devices. Delivery conduit 6 is structured to communicate the flow of breathing gas from pressure generating device 4 to patient interface device 8. Delivery conduit 6 and patient interface device 8 are often collectively referred to as a patient circuit.

A BiPAP device is a bi-level device in which the pressure provided to the patient varies with the patient's respiratory cycle, so that a higher pressure is delivered during inspiration than during expiration. An auto-titration pressure support system is a system in which the pressure varies with the condition of the patient, such as whether the patient is snoring or experiencing an apnea or hypopnea. For present purposes, pressure/flow generating device 4 is also referred to as a gas flow generating device, because flow results when a pressure gradient is generated. The present invention contemplates that pressure/flow generating device 4 is any conventional system for delivering a flow of gas to an airway of a patient or for elevating a pressure of gas at an airway of the patient, including the pressure support systems summarized above and non-invasive ventilation systems.

In the illustrated example system 2 of FIG. 1, patient interface device 8 is depicted as a nasal/oral mask which includes a patient sealing assembly in the form of a cushion 12 coupled to a generally rigid frame member of faceplate 14 which may be coupled to conduit 6 either directly or indirectly via any suitable coupling mechanism. However, any type of patient interface device 8, such as, without limitation, a nasal mask that covers the patient's nose, a nasal cushion having nasal prongs that are received within the patient's nares, or a full face mask that covers the patient's face, which facilitates the delivery of the flow of breathing gas to, and the removal of a flow of exhalation gas from, the airway of a patient may be used while remaining within the scope of the present disclosed concept.

Figure 2:
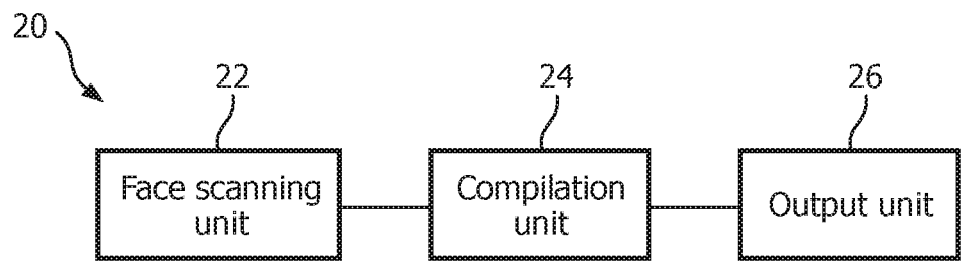
FIG. 2 is a schematic diagram of an electronic apparatus for determining additional information about a patient's face according to an exemplary embodiment of the disclosed concept.

A schematic diagram of an electronic apparatus 20 for determining additional information about the patient's face is shown in FIG. 2. The additional information is information in addition to the external geometry of the patient's face and may include, without limitation, information on a location of hard tissue (e.g. without limitation, skeletal structure), a depth of soft tissue and a compliance of soft tissue and/or hard tissue in the patient's face.

Electronic apparatus 20 includes a face scanning unit 22, a compilation unit 24 and an output unit 26. Face scanning unit 22, compilation unit 24 and output unit 26 may share a housing and form a single device. However, it is also contemplated that face scanning unit 22, compilation unit 24 and output unit 26 may be located in different housings in different devices without departing from the scope of the disclosed concept.

Face scanning unit 24 is structured to generate 3-D models of the patient's face by, for example, scanning the patient's face. Face scanning unit 22 may be, without limitation, a 3-D optical scanner, a camera, a push-pin array or any other device suitable for generating 3-D models of the patient's face. Face scanning unit 22 is structured to generate multiple 3-D models of the patient's face by, for example, scanning the patient's face at different times. Face scanning unit 22 is structured to output the different 3-D models of the patient's face to compilation unit 24.

Compilation unit 24 is structured to receive multiple different 3-D models of the patient's face from face scanning unit 22. For example, in a first 3-D model of the patient's face, the patient's face is not manipulated during scanning, whereas in a second 3-D model of the patient's face, the patient's face is manipulated in some manner during scanning so that the first 3-D model of the patient's face and the second 3-D model of the patient's face are different.

Figure 3A:
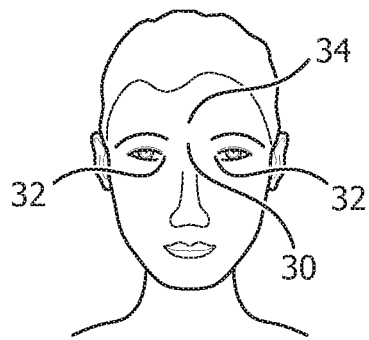
FIGS. 3A and 3B are images of a patient's face with different expressions.
Figure 3B:
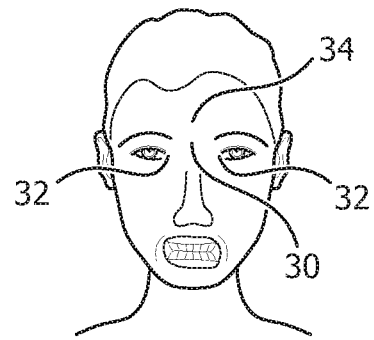

Referring to FIGS. 3A and 3B, an example of manipulation of the patient's face in accordance with an exemplary embodiment of the disclosed concept is shown. FIG. 3A shows the patient's face during generation of a first 3-D model of the patient's face. As shown in FIG. 3A, the patient's mouth is closed. FIG. 3B shows the patient's face during generation of a second 3-D model of the patient's face. As shown in FIG. 3B, the patient's face is manipulated by having the patient open his mouth and show his teeth. Thus, the first and second 3-D models of the patient's face are different due to manipulating the patient's face.

Referring back to FIG. 2, compilation unit 24 is structured to compare different 3-D models of the patient's face. From the comparison, compilation unit 24 determines additional information about the patient's face. As previously mentioned, the additional information is information in addition to the external geometry of the patient's face and may include, for example and without limitation, information about a location of hard tissue, a depth of soft tissue and a compliance of soft tissue and/or hard tissue in the patient's face.

In some exemplary embodiments of the disclosed concept, compilation unit 24 is structured to compare the different 3-D models of the patients face by correlating the different 3-D models of the patient's face. The compilation unit 24 may detect anatomical landmarks on the patient's face to facilitate the correlation. Some anatomical landmarks such as, without limitation, the sellion, eye corners and glabella remain unchanged even when a patient changes expressions. Thus, these landmarks can be used to correlate different 3-D models of the patient's face where the patient changes expressions between 3-D models.

Figure 3C:
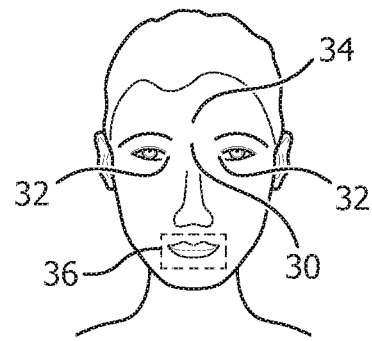
FIG. 3C shows a result of correlating the images of FIGS. 3A and 3B in accordance with an exemplary embodiment of the disclosed concept.

FIGS. 3A-3C illustrate an example of how different 3-D models of the patient's face can be correlated to determine additional information about the patient's face. FIGS. 3A and 3B illustrate that patient's face during generation of different 3-D models of the patient's face. Although the patient's expression changes between FIGS. 3A and 3B, some anatomical landmarks such as the sellion 30, eye corners 32 and glabella 34 do not change position. Compilation unit 24 may detect and use these landmarks to correlate different 3-D models of the patient's face. Although the sellion 30, eye corners 32 and glabella 34 are illustrated as example landmarks, it will be appreciated by those having ordinary skill in the art that other landmarks may be detected and used by compilation unit 24 without departing from the scope of the disclosed concept. For example and without limitation, in an exemplary embodiment of the disclosed concept, the outer or center part of the eye, the nose tip, and/or the mouth corners are landmarks that are detected and used by compilation unit 24. Landmarks that are further from each other allow more accurate tracking of the head position and also, as the distance between landmarks becomes greater, the stability of the landmarks with respect to changes in facial expression become less important.

FIG. 3C illustrates a representation of a correlation of different 3-D models of the patient's face obtained from scanning the patient's face as shown in FIGS. 3A and 3B. From correlating the different 3-D models of the patient's face, additional information about the patient's face such as information on the location of hard tissue underlying soft tissue in the patient's face (e.g., without limitation, the location of the patient's teeth) may be determined. The additional information is represented as an outline 36 in FIG. 3C. However, it will be appreciated by those having ordinary skill in the art that the additional information may be provided in any suitable manner such as, without limitation, in image form or in raw data form.

Referring back to FIG. 2, compilation unit 24 is structured to output the additional information about the patient's face to output unit 26. Output unit 26 is structured to output the additional information to a user of system 20 such as a caregiver, patient interface device manufacturer or any other entity that has use for the additional information. Output unit 26 may be any suitable device for outputting the additional information in a useful manner such as, without limitation, a display device. It is also contemplated that output unit 26 may output data (e.g., without limitation, a 3-D geometry file) that can be used, for example and without limitation, in the construction or fitting of a patient interface device. It is further contemplated that in some exemplary embodiments of the disclosed concept, output unit 26 may output data to a remote storage location (e.g., without limitation, cloud-based storage) via a network connection.

The additional information is useful in determining an optimally fitting patient interface device for the patient. Additional information such as, without limitation, the location of hard tissue, the depth of soft tissue and the compliance of soft tissue and/or hard tissue can affect how a patient interface device fits a patient. For example, an area of a patient's face where hard tissue is located and the soft tissue has little depth or compliance can be a concern for irritation if a patient interface applied pressure to that area. The additional information can be used to select and/or design a patient interface device that does not apply pressure, or applies less pressure, to an area of the patient's face where hard tissue is located and the depth and compliance of soft tissue are low, thus resulting in a better fit of the patient interface device than if it were selected or designed based on the external geometry of the patient's face alone. Algorithms that determine the fit between a patient interface device and the patient can employ the additional information in order to more accurately optimize the fit of a patient interface device for a patient.

It is contemplated that the additional information may be used to select, adjust or customize a patient interface device for the patient that optimally fits the patient. Furthermore, it is contemplated that the additional information may be used to create a custom patient interface device for the patient that optimally fits the patient.

Figure 4:
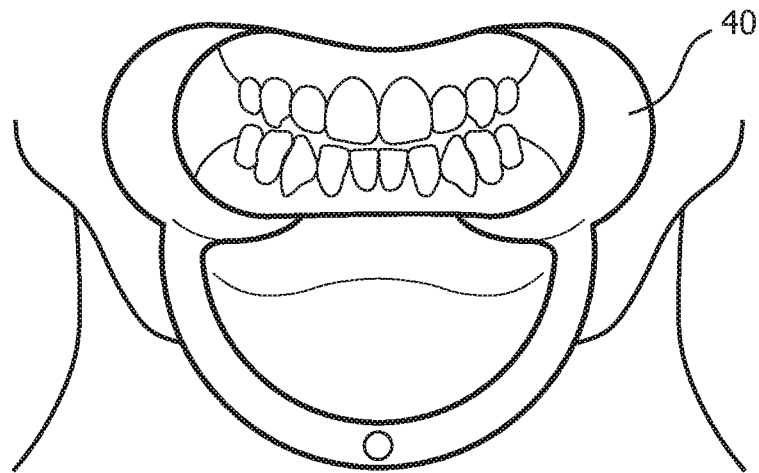
FIG. 4 is an image an image of a patient's face that is manipulated with a lip retractor in accordance with an exemplary embodiment of the disclosed concept.

It is contemplated that the patient's face may be manipulated in any suitable manner to generate the different 3-D models of the patient's face. As shown in FIGS. 3A-3C, the patient's face is manipulated by having the patient change expressions to expose their teeth allows the compilation. A variation of this type of manipulation is shown in FIG. 4. As shown in FIG. 4, rather than having the patient change expressions to expose their teeth, the patient's face is manipulated by having the patient's use a lip retractor 40 is used to expose the patient's teeth.

In some other example embodiments of the disclosed concept, the patient's face is manipulated by using airflow. In some example embodiments of the disclosed concept, the patient's face is manipulated by placing the patient in a wind tunnel and allowing the airflow of the wind to deform the patient's face. In some other example embodiments of the disclosed concept, an airflow is generated and blown only towards selected areas of the patient's face.

Figure 5:
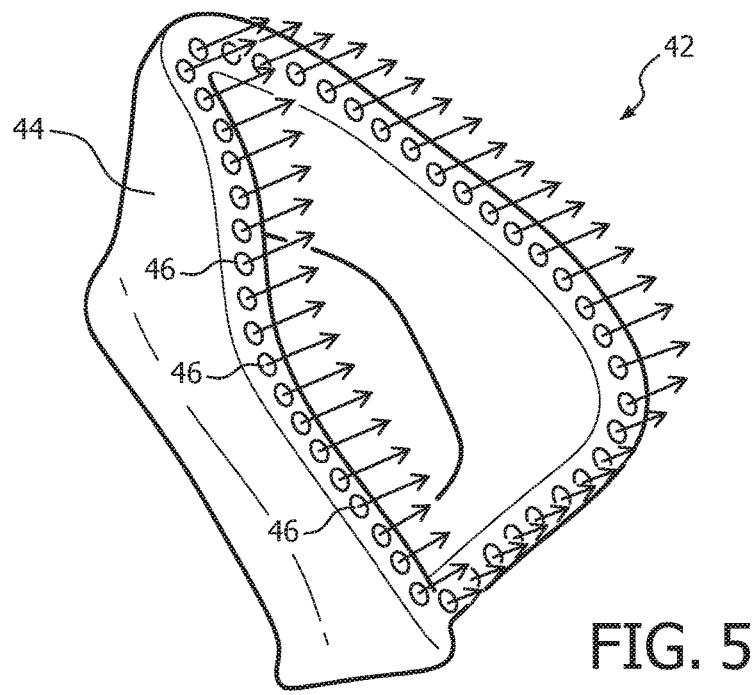
FIG. 5 is an isometric view of an air cushion in accordance with an exemplary embodiment of the disclosed concept.

FIG. 5 illustrates an air cushion 42 in accordance with an example embodiment of the disclosed concept. Air cushion 42 includes a body 44. Body 44 generally has the shape of a cushion of a patient interface device. However, it will be appreciated by those having ordinary skill in the art that body 44 may have a different shape (e.g., without limitation, a flat contour) without departing from the scope of the disclosed concept. Numerous apertures 46 are formed in a side of body 44 that will face the patient's face. Body 44 is structured to be connected to an air blower (not shown) that will generate air pressure that passes through body 44 and out of apertures 46. Although an air blower is not shown in FIG. 5 it will be appreciated by one having ordinary skill in the art that any suitable air blower may be employed such as an air blower similar to air blower 54 or an air blower that that provides a higher air pressure than what is normally provided by a CPAP machine. When air cushion 42 is placed near the patient's face, the air blowing from apertures 46 will manipulate the patient's face by causing the patient's face to deform in the vicinity of apertures 46. Manipulating the patient's face by using airflow can provide additional information on, without limitation, a location of hard tissue, a depth of soft tissue and a compliance of soft and/or hard tissue in the patient's face.

Figure 6:
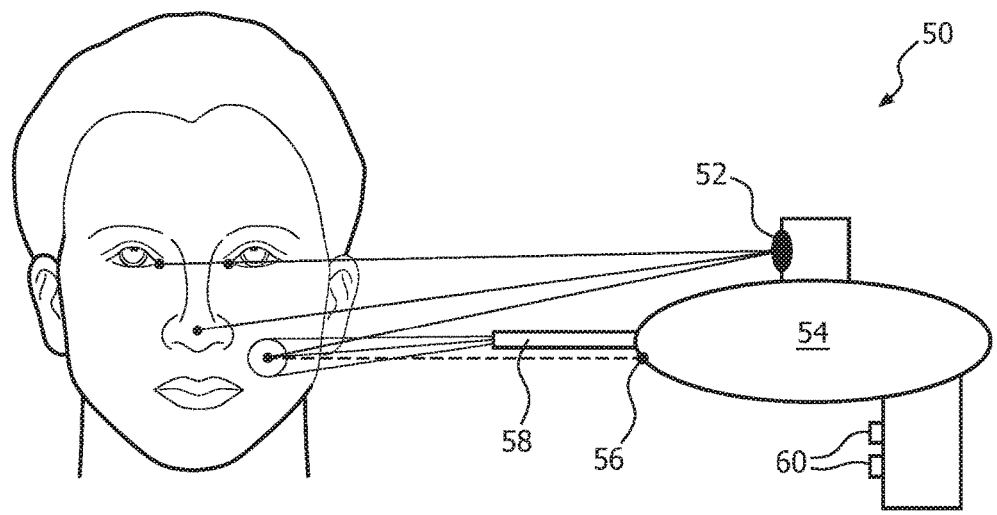
FIG. 6 is a schematic diagram of a modified face scanning unit in accordance with an exemplary embodiment of the disclosed concept.

FIG. 6 is a schematic diagram of a modified face scanning unit 50 in accordance with another example embodiment of the disclosed concept. The modified face scanning unit 50 includes a 3-D camera 52, an air blower 54 and a laser pointer 56.

Modified face scanning unit 50 is structured to generate different 3-D models of the patient's face. To this extent, 3-D camera 52 takes 3-D images of the patient's face for use in generating 3-D models of the patient's face. Air blower 54 is structured to generate airflow in the direction of the patient's face. The airflow manipulates the patient's face by causing deformation of a portion of the patient's face. By taking a 3-D images of the patient's face when air blower 54 is not generating airflow to manipulate a portion of the patient's face and taking another 3-D image when air blower 54 is generating airflow to manipulate a portion of the patient's face, different 3-D models of the patient's face can be generated by modified face scanning unit 50.

Air blower 54 may be any device suitable for generating airflow and blowing the air on a portion of the patient's face. In some exemplary embodiments of the disclosed concept, an air directing member 58, such as a conduit, may be attached to air blower 54 in order to facilitate directing the airflow to a selected portion of the patient's face. In some exemplary embodiments of the disclosed concept, air blower 54 is structured to modulate the airflow by, for example and without limitation, periodically increasing and decreasing the amplitude of the generated airflow. The modulated airflow causes variations in the deformation of the patient's face, which can assist in determining additional information about the patient's face when different 3-D models of the patient's face are compared.

Laser pointer 56 is structured to generate a laser dot on the patient's face in the area where air blower 54 is blowing air on the patient's face. The laser dot can be used to triangulate the distance from air blower 54 to the patient's face to more accurately calculate the position of air blower 54. Additionally, the modulated airflow generated by air blower 54 will cause lateral oscillations of the laser dot on the patient's face. The amplitude and frequency of these oscillations can be translated into additional information about the patient's face such as, without limitation, depth fluctuations of soft tissue in the area of the airflow which indicate properties of the soft tissue, such as depth and compliance.

Modified face scanning unit 50 may further include control buttons 60. A user of modified face scanning unit 50 may use control buttons 60 to operate or adjust setting of modified face scanning unit 50.

Modified face scanning unit 50 may be used in conjunction with compilation unit 24 previously described and shown in FIG. 2. The different 3-D models of the patient's face generated by modified face scanning unit 50 may be input into compilation unit 24. Compilation unit 24 is structured to compare the different 3-D models of the patient's face, such as the different 3-D models of the patient's face generated by modified face scanning unit 50, and determine additional information about the patient's face from the comparison. It is contemplated that in some exemplary embodiments of the disclosed concept that modified face scanning unit 50 and compilation unit 24 are included together in a single device. It is also contemplated that output unit 26 may be included with modified face scanning unit 50 and compilation unit 24 in a single device.

In addition to the manners of manipulating the patient's face that have already been described, it is contemplated that the patient's face may be manipulated in any suitable manner without departing from the scope of the disclosed concept. For example and without limitation, the patient's face may also be manipulated by pressing on the patient's face, having the patient change expressions in any suitable manner (e.g., without limitation, having a patient blow up or suck in their cheeks) or having the patient change positions (e.g., without limitation, standing up and laying down) to have the changed effect of gravity manipulate the patient's face.

Figure 7:
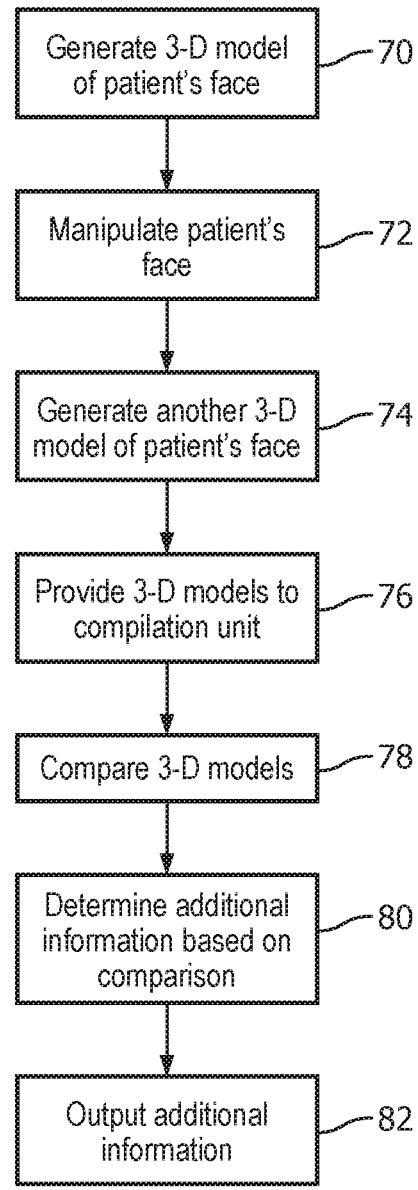
FIG. 7 is a flowchart of a method of determining additional information about a patient's face in accordance with an exemplary embodiment of the disclosed concept.

FIG. 7 is a flowchart of a method of determining additional information about a patient's face in accordance with an exemplary embodiment of the disclosed concept. The method of FIG. 7 may be implemented in the electronic apparatus 20 shown in FIG. 2. However, it will be appreciated by those having ordinary skill in the art that the method of FIG. 7 may be employed in conjunction with other devices without departing from the scope of the disclosed concept.

In operation 70, a 3-D model of the patient's face is generated. The 3-D model may be generated using any suitable type of device such as, without limitation, the face scanning unit 22 of FIG. 2 or the modified face scanning unit 50 of FIG. 6. In operation 70, the patient's face is manipulated in some manner. The patient's face may be manipulated in any manner such as, without limitation, changing expression, using airflow, using a device such as a lip retractor, pressing on the patient's face, or any other suitable manner of manipulating the patient's face. In operation 74, another 3-D model of the patient's face, which is different than the first 3-D model of the patient's face, is generated while the patient's face is manipulated. It will be appreciated by those having ordinary skill in the art that operations 72 and 74 may be repeated to generate any number of different 3-D models of the patient's face without departing from the scope of the disclosed concept.

In operation 76, the different 3-D models of the patient's face are provided to a compilation unit such as compilation unit 24 shown in FIG. 2. In operation 78, the different 3-D models of the patient's face are compared to each other. In some exemplary embodiments of the disclosed concept, the 3-D models of the patient's face are compared to each other by correlating them with each other based on landmarks on the patient's face. For example and without limitation, landmarks on a patient's face that do not change with manipulation of the patient's face may be used to align the 3-D models of the patient's face. Once the 3-D models are aligned, their surfaces can be compared in the depth direction to, for example, determine how thick soft tissue is in areas of the patient's face. In operation 80, additional information about the patient's face is determined based on the comparison. The additional information is information in addition to the external geometry of the patient's face and may include, without limitation, a location of hard tissue, depth of soft tissue and compliance of soft tissue. Finally, in operation 82, the additional information is output. The additional information may be output in any useful manner such as, without limitation, displaying the additional information or outputting data including the additional information (e.g., without limitation, a computer readable file).

The present disclosed concept can be embodied in an electronic apparatus, such as, for example and without limitation, a mobile device, a mobile computer, a tablet computer, a peripheral device etc. The present disclosed concept can also be embodied as computer readable codes on a tangible computer readable recording medium. The computer readable recording medium is any data storage device that can store data which can be thereafter read by a computer system. Examples of the computer readable recording medium include read-only memory (ROM), random-access memory (RAM), CD-ROMs, magnetic tapes, floppy disks, and optical data storage devices.

It is contemplated that the additional information determined about a patient face in conjunction with any of the embodiments, combination of embodiments, or modification of embodiments of the disclosed concept described herein can be used by, for example and without limitation, a caregiver, technician, or patient in the process of selecting a patient interface device, adjusting a patient interface device, customizing a patient interface device or creating a patient interface device.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. An electronic apparatus comprising:
   an air blower structured to generate an airflow that applies pressure to a patient's face;
   a face scanning unit structured to generate a plurality of 3-D models of the patient's face, wherein the plurality of 3-D models comprises at least a first 3-D model of the patient's face in an absence of the airflow, and a second 3-D model of the patient's face when the airflow is applying pressure to the patient's face; and
   a compilation unit structured to:
      receive the plurality of 3-D models, and
      determine additional information about the patient's face based on a comparison of the plurality of 3-D models,
   wherein the additional information includes at least one of a location of hard tissue, a depth of soft tissue, and a compliance of soft tissue and/or hard tissue.

2. The electronic apparatus of claim 1, further comprising: an output unit structured to provide the additional information to a user.

3. The electronic apparatus of claim 1, wherein the compilation unit is structured to correlate the plurality of 3-D models of the patient's face based on landmarks on the patient's face.

4. The electronic apparatus of claim 3, wherein the landmarks include at least one of a sellion, eye corners and a glabella.

5. The electronic apparatus of claim 1, wherein:
   in a third 3-D model of the patient's face, the patient's teeth are shown, and
   in a fourth 3-D model of the patient's face, the patient's teeth are not shown.

6. The electronic apparatus of claim 5, wherein a lip retractor is used to show the patient's teeth.

7. The electronic apparatus of claim 1, further comprising:
   an air cushion having a body in a shape of a cushion of a patient interface device and including a plurality of apertures formed therein, wherein the air cushion is structured to provide the airflow generated by the air blower to the patient's face through the plurality of apertures.

8. The electronic apparatus of claim 1, further comprising:
   a laser pointer structured to generate a laser dot on the patient's face in an area where the airflow is applying pressure to the patient's face.

9. The electronic apparatus of claim 1, wherein the air blower is structured to modulate the airflow.

10. The electronic apparatus of claim 1, wherein the patient's face is manipulated by the airflow applying pressure to one or more portions of the patient's face.

11. A method implemented on a computer system comprising a non-transitory computer readable medium having computer code stored thereon for determining additional information about a patient's face, the method comprising:
    generating a first 3-D model of a patient's face;
    generating an airflow that applies pressure to the patient's face;
    generating at least a second 3-D model of the patient's face when the airflow is applying pressure to the patient's face;
    and
    determining additional information about the patient's face based on a comparison of the first 3-D model and at least the second 3-D model,
    wherein the additional information includes at least one of a location of hard tissue, a depth of soft tissue and a compliance of soft tissue and/or hard tissue.

12. The method of claim 11, wherein the second 3-D model is generated for the airflow applying pressure to a first portion of the patient's face, the method further comprises:
    causing the airflow to apply pressure to a second portion of the patient's face; and
    generating a third 3-D model of the patient's face, wherein the additional information is determined based on the first 3-D model, the second 3-D model, and the third 3-D model being compared.

13. The method of claim 11, wherein determining the additional information based on the comparison comprises:
    correlating the first 3-D model and at least the second 3-D model based on landmarks on the patient's face.

14. The method of claim 11, wherein:
    in a third 3-D model of the patient's face, the patient's teeth are shown, and
    in a fourth 3-D model of the patient's face, the patient's teeth are not shown, such that the additional information is further determined based on the third 3-D model and the fourth 3-D model.

15. The method of claim 11, wherein the airflow is provided through an air cushion having a body in a shape of a cushion of a patient interface device and including a plurality of apertures formed therein.

16. The method of claim 11, further comprising:
generating a laser dot on the patient's face in an area where the airflow is applying pressure to the patient's face;
modulating the airflow to cause oscillations of the laser dot on the patient's face, wherein the additional information is determined based on an amplitude and a frequency of the oscillations.

17. The method of claim 11, wherein the patient's face is manipulated by the airflow applying pressure to one or more portions of the patient's face.

18. The electronic apparatus of claim 8, wherein the air blower is further structured to:
modulate the airflow to cause oscillations of the laser dot on the patient's face, wherein the additional information is determined based an amplitude and frequency of the oscillations.

19. The electronic apparatus of claim 18, wherein:
the plurality of 3-D models further comprises at least a third 3-D model of the patient's face;
the second 3-D model corresponding to the airflow applying pressure to a first portion of the patient's face and the third 3-D model corresponding to the airflow applying pressure to at a second location of the patient's face; and
the air blower being structured to modulate the airflow comprises the air blower generating the airflow having a first amplitude when applying pressure to the first location and a second amplitude when applying pressure to the second location, wherein the additional information is determined based on the first 3-D model, the second 3-D model, and the third 3-D model.

20. The electronic apparatus of claim 1, further comprising an output unit structured to output data used to construct a patient interface device for the patient based on the additional information.

21. The method of claim 16, further comprising:
modulating the airflow such that the airflow has a first amplitude when applying pressure to a first location of the patient's face, wherein the second 3-D model is generated for the airflow applying pressure to the first location of the patient's face;
modulating the airflow such that the airflow has a second amplitude when applying pressure to a second location of the patient's face;
generating a third 3-D model of the patient's face when the airflow is applying pressure to the second location of the patient's face, wherein the additional information is determined based on the first 3-D model, the second 3-D model, and the third 3-D model.

* * * * *